United States Patent
Cepla et al.

(10) Patent No.: US 11,186,784 B2
(45) Date of Patent: Nov. 30, 2021

(54) DEHYDROGENATION PROCESS HAVING IMPROVED RUN TIME

(71) Applicant: UOP LLC, Des Plaines, IL (US)

(72) Inventors: Alan E. Cepla, Hawthorn Woods, IL (US); Gary A. Dziabis, Addison, IL (US); Manuela Serban, Northbrook, IL (US); Rui de Menezes, Goa (GB); Massimiliano Cantarelli, Milan (IT)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 16/513,656

(22) Filed: Jul. 16, 2019

(65) Prior Publication Data
US 2020/0115641 A1    Apr. 16, 2020

Related U.S. Application Data

(60) Provisional application No. 62/745,665, filed on Oct. 15, 2018.

(51) Int. Cl.
*C10G 49/14* (2006.01)
*B01J 8/00* (2006.01)
*B01J 8/24* (2006.01)
*C07C 5/32* (2006.01)
*G06Q 10/10* (2012.01)

(52) U.S. Cl.
CPC .............. *C10G 49/14* (2013.01); *B01J 8/001* (2013.01); *B01J 8/0015* (2013.01); *B01J 8/24* (2013.01); *C07C 5/32* (2013.01); *G06Q 10/1097* (2013.01); *B01J 2208/00707* (2013.01); *C10G 2300/1081* (2013.01); *C10G 2300/4081* (2013.01); *C10G 2400/20* (2013.01)

(58) Field of Classification Search
CPC .... C10G 49/14; B01J 8/00; B01J 8/24; G06Q 10/10
See application file for complete search history.

(56) References Cited

U.S. PATENT DOCUMENTS

| | | | |
|---|---|---|---|
| 3,491,162 A | 1/1970 | Bloch | |
| 3,760,168 A * | 9/1973 | Boyd | C07C 5/333 700/272 |
| 5,324,880 A | 6/1994 | Dyroff | |
| 5,486,348 A * | 1/1996 | Verduijn | B01J 29/60 423/700 |
| 7,235,706 B2 * | 6/2007 | Iezzi | B01J 8/0055 585/654 |
| 2002/0001642 A1 | 11/2002 | Cottrell | |
| 2014/0273794 A1* | 9/2014 | Fridman | B01J 8/0496 454/237 |

FOREIGN PATENT DOCUMENTS

| | | |
|---|---|---|
| EP | 0431732 A1 | 6/1991 |
| RU | 2160698 C1 | 12/2000 |
| WO | WO2016170450 | 10/2016 |

OTHER PUBLICATIONS

Rahimpour et al. (Progress in catalytic naphtha reforming process: A review, Applied Energy 109 (2013) pp. 79-93) (Year: 2013).*

* cited by examiner

*Primary Examiner* — Youngsul Jeong
(74) *Attorney, Agent, or Firm* — Paschall & Associates, LLC; Mark Goldberg

(57) ABSTRACT

New/fresh catalyst is added to a dehydrogenation unit and aged catalyst is removed from the dehydrogenation unit on a continuous or semi-continuous basis while the dehydrogenation unit is in operation. The conversion achieved by the higher activity catalyst results in the production rate of olefin product being maintained at near start-of-run production for longer, with a slower rate of decline. The higher activity catalyst extends run time, reduces feed consumption for each unit of olefin product, and minimizes fresh catalyst expenses.

17 Claims, No Drawings

DEHYDROGENATION PROCESS HAVING IMPROVED RUN TIME

CROSS-REFERENCE TO RELATED APPLICATION

This application claims priority from Provisional Application No. 62/745,665 filed Oct. 15, 2018, the contents of which cited application are hereby incorporated by reference in its entirety.

BACKGROUND

The dehydrogenation of hydrocarbons is an important commercial hydrocarbon conversion process because of the existing and growing demand for dehydrogenated hydrocarbons for the manufacture of various chemical products such as detergents, high octane gasolines, oxygenated gasoline blending components, pharmaceutical products, plastics, synthetic rubbers, and other products which are well known to those skilled in the art. One example of this process is the dehydrogenation of propane to produce propylene which is polymerized to provide a material used in a wide variety of products including utensils, clothing, rugs, packaging, and vehicle batteries and bumpers. Another example of this process is the dehydrogenation of isobutane to produce isobutylene which can be polymerized to provide tackifying agents for adhesives, viscosity-index additives for motor oils, and impact-resistant and antioxidant additives for plastics. Another example of the growing demand for isobutylene is the production of oxygen-containing gasoline blending components which are being mandated by the government in order to reduce air pollution from automotive emissions.

Those skilled in the art of hydrocarbon conversion processing are well versed in the production of olefins by means of catalytic dehydrogenation of paraffinic hydrocarbons. In addition, many patents have issued which teach and discuss the dehydrogenation of hydrocarbons in general. For example, U.S. Pat. No. 4,430,517 (Imai et al) discusses a dehydrogenation process and catalyst for use therein.

The performance of dehydrogenation units is detrimentally impacted by deactivation of the catalyst. The reactor screens that contain the catalyst bed in an annular region of the reactor tend to foul with carbonaceous byproducts of the dehydrogenation reactions. As the catalyst deactivates over months or years of service, the operating temperature of the catalyst increases, and the formation of byproducts worsens. It has been observed that the fouling rate tends to accelerate as the catalyst ages. This means that the dehydrogenation unit performance is declining far more rapidly in the last year of a multi-year run than in the first year.

The screen fouling also causes an increase in the average reactor pressure which is unfavorable for the desired dehydrogenation reactions, causing a decline in conversion at constant reactor inlet temperature. Because dehydrogenation reactions result in an increase in number of moles, they are negatively impacted by an increase in pressure. Over a typical run, there is decline in performance seen over time, which has traditionally been attributed to loss of catalyst activity. However, a more detailed analysis reveals that only part of the performance decline is directly due to the activity of the catalyst, with the pressure profile through the reactor being the other significant factor. Over time during the run, the increased pressure drop in the process gas circulation loop that circulates the reactants through the dehydrogenation reactor results in a reduction in the maximum extent of propane conversion from the desired dehydrogenation reaction at constant reactor inlet temperatures. This causes a reduction in the propylene production rate and an increase in the quantity of propane consumed in producing each ton of propylene product.

In addition, the catalyst deactivation itself also causes a further decline in conversion, requiring an increase in the operating temperature. This results in an increase in feed consumption due to thermal cracking, resulting in a decline in olefin production rate. As a result, the rate of screen fouling accelerates, eventually requiring the dehydrogenation unit to be shut-down to clean the screens. This negatively impacts the economics of the operation because of lost production and higher maintenance costs.

One solution to catalyst deactivation has been to replace the entire catalyst inventory, but only after significant decline in activity. To reduce the rate of screen fouling and improve production and propane consumption, operators replace the entire load of catalyst on a more frequent basis and before the catalyst activity declines below a critical threshold that results in the adverse consequences discussed above. However, this option results in higher operating costs because of the cost of the more frequent catalyst replacement. It is also normal practice to continuously remove catalyst fines or broken particles from the circulating catalyst via elutriation. However, the quantity of these small particles removed via elutriation, and subsequently replaced with fresh catalyst, is too little to maintain the catalyst activity above the critical threshold that results in the adverse consequences discussed above. This elutriation system is optimized to remove particle sizes below 75% of the normal/nominal catalyst particle size. By way of example, the elutriation would target removal of particles less than or equal to 1.2 mm when the nominal catalyst particle size is 1.6 mm in diameter.

Therefore, it is desirable to reduce screen fouling and increase the time between reactor shutdowns.

SUMMARY AND DETAILED DESCRIPTION

In the new process, new/fresh catalyst is added to the dehydrogenation unit and aged catalyst is removed from the dehydrogenation unit on a continuous or semi-continuous basis while the dehydrogenation unit is in operation. One or more "on-the-fly" catalyst changes are performed at intervals between successive reactor shut-downs with a view to reducing the rate of fouling by carbonaceous material, and consequently extending the interval between successive turnarounds. Unlike the prior art process, the new process does not target catalyst removal due to small particle size, but instead removes catalyst in the typical/nominal size range and replaces with fresh/new catalyst of the same size.

The new process economically maintains the dehydrogenation catalyst inventory above an activity level that is high enough to provide multiple valuable benefits. Reactor screen fouling rates are slowed, so that the time between shutdowns to clean the reactors screens is extended. The conversion achieved by the higher activity catalyst results in the production rate of olefin product (e.g., propylene or isobutylene) being maintained at near start-of-run production for longer, with a slower rate of decline. The higher activity catalyst also results in reduced feed consumption for each unit of olefin product. It also minimizes the fresh catalyst expenses.

The portion of catalyst removed and replaced with fresh catalyst is generally in the range of between 5% and 50% of the total amount of catalyst in the unit. The frequency of replace is generally between one time about every 45 days to one time about every 180 days. Replacement rates outside this range are either ineffective or are less economical.

Approximately 6-12 months before the planned shutdown of the dehydrogenation unit for regular maintenance and for a complete catalyst change-out, the catalyst replacement is stopped. This reduces the catalyst expense while still allowing the operator to reach the desired time before dehydrogenation unit maintenance.

Early catalyst replacement reduces the rate of carbonaceous fouling, and consequently lowers the rate of increase in pressure drop across the reactor outer screens. As the pressure drop across the outer screens of downstream reactors typically determines turnaround frequency, this change allows longer operating time between successive turnarounds. Rather than using an arbitrary drop in propylene yield per pass (e.g., 5%) to determine catalyst life, catalyst replacement frequency is determined based on targeting an economic optimum.

In some embodiments, the rate of catalyst replacement is between 10-20 wt % of the entire catalyst inventory being replaced with fresh catalyst every 60-120 operating days. In some embodiments, about 15 wt % should be replaced every 90 operating days. This rate results in maintaining the catalyst activity index in the desired range to significantly slow screen fouling rates and achieve a 20-100% longer time between shutdowns for screen cleaning.

The catalyst being replaced has a particle size in the normal operating range for that particular catalyst. By the "particle size in the normal operating range," we mean the particle size is within 25% of the nominal particle size of the catalyst, or within 20%, or within 15%, or within 10%, or within 5%.

One aspect of the invention is a process for dehydrogenation of a hydrocarbon feed. In one embodiment, the process comprises providing a hydrocarbon feed stream comprising at least one paraffin to a dehydrogenation unit comprising a moving bed reactor. The feed stream is contacted with a catalyst in the reactor under dehydrogenation conditions, the catalyst having a particle size in a normal operating range. An effluent stream comprising at least one olefin is removed from the reactor. A portion of the catalyst is periodically removed and replaced with fresh catalyst while continuing to operate the reactor, wherein the portion of the catalyst removed has a particle size in the normal operating range.

In some embodiments, the portion of the catalyst removed is between 5 wt % and 50 wt % of a total amount of the catalyst in the dehydrogenation unit.

In some embodiments, the portion of the catalyst is removed on a predetermined time schedule.

In some embodiments, the portion of the catalyst removed and replaced is between 10 wt % and 20 wt % of a total amount of the catalyst in the dehydrogenation unit.

In some embodiments, the catalyst is removed and replaced every 60 to 120 days of operating time.

In some embodiments, removing the portion of the catalyst and replacing the portion of the catalyst removed with fresh catalyst is stopped at a predetermined time before a planned shutdown of the reactor.

In some embodiments, the predetermined time is 6 to 12 months before the planned shutdown of the reactor.

In some embodiments, an operating time for the reactor is increased at least 20% over an operating time for the reactor without removing the portion of the catalyst and replacing the portion of the catalyst removed with fresh catalyst.

In some embodiments, the portion of the catalyst removed is determined by one or more of: measuring a production rate of the at least one olefin; measuring a consumption rate of the hydrocarbon feed; measuring a cost of the fresh catalyst replaced; measuring a temperature decrease across the reactor; or measuring a concentration of the at least one paraffin or the at least one olefin or both at an outlet of the reactor.

In some embodiments, the process further comprises at least one of: sensing at least one parameter of the process and generating a signal or data from the sensing; generating and transmitting a signal; or generating and transmitting data.

Another aspect of the invention is a process for dehydrogenation of a hydrocarbon feed. In one embodiment, the process comprises: providing a hydrocarbon feed stream comprising at least one paraffin to a dehydrogenation unit comprising a moving bed reactor; contacting the feed stream with a catalyst in the reactor under dehydrogenation conditions; removing an effluent stream comprising at least one olefin from the dehydrogenation unit; and periodically removing between 5 wt % and 50 wt % of a total amount of the catalyst in the reactor every 60 to 120 days of operating time and replacing the removed catalyst with fresh catalyst while continuing to operate the reactor.

In some embodiments, the portion of the catalyst removed and replaced is between 10 wt % and 20 wt % of a total amount of the catalyst in the dehydrogenation unit.

In some embodiments, removing the portion of the catalyst and replacing the portion of the catalyst removed with fresh catalyst is stopped at a predetermined time before a planned shutdown of the reactor.

In some embodiments, the predetermined time is 6 to 12 months before the planned shutdown of the reactor.

In some embodiments, an operating time for the reactor is increased at least 20% over an operating time for the reactor without removing the portion of the catalyst and replacing the portion of the catalyst removed with fresh catalyst.

In some embodiments, the portion of the catalyst removed is determined by one or more of: measuring a production rate of the at least one olefin; measuring a consumption rate of the hydrocarbon feed; or measuring a cost of the fresh catalyst replaced.

Another aspect of the invention is a process for dehydrogenation of a hydrocarbon feed. In one embodiment, the process comprises: providing a hydrocarbon feed stream comprising at least one paraffin to a dehydrogenation unit comprising a moving bed reactor; contacting the feed stream with a catalyst in the reactor under dehydrogenation conditions; removing an effluent stream comprising at least one olefin from the reactor; and periodically removing between 10 wt % and 20 wt % of a total amount of the catalyst in the dehydrogenation unit every 60 to 120 days of operating time and replacing the removed catalyst with fresh catalyst while continuing to operate the reactor.

In some embodiments, removing the portion of the catalyst and replacing the portion of the catalyst removed with fresh catalyst is stopped 6 to 12 months before the planned shutdown of the reactor.

Another aspect of the invention is a process for dehydrogenation of a hydrocarbon feed. In one embodiments, the process comprises: providing a hydrocarbon feed stream comprising at least one paraffin to a dehydrogenation unit comprising a moving bed reactor; contacting the feed stream with a catalyst in the reactor under dehydrogenation conditions; removing an effluent stream comprising at least one olefin from the reactor; periodically removing a portion of the catalyst in the reactor and replacing the removed catalyst with fresh catalyst while continuing to operate the reactor; sensing one or more of a flow rate of the feed stream, or a flow rate of the effluent; transmitting one or more of the flow rate of the feed stream, or the flow rate of the effluent to a processor; analyzing one or more of the flow rate of the feed stream, or the flow rate of the effluent to determine an activity rate; analyzing the activity rate and a cost of the catalyst to determine at least one of an amount of catalyst to remove and replace, or a time to initiate removing and replacing the catalyst; and adjusting the portion of the catalyst removed and replaced to the determined amount of catalyst, or removing and replacing the catalyst at the determined time.

The dehydrogenation of paraffinic hydrocarbons is well known to those skilled in the art of hydrocarbon processing. Dehydrogenatable hydrocarbons are contacted with the catalytic composition described above in a dehydrogenation zone maintained at dehydrogenation conditions. This contacting may be accomplished in a fixed catalyst bed system, a moving catalyst bed system, a fluidized bed system, etc., or in a batch-type operation. The dehydrogenation unit may comprise one or more separate reactors with heating means therebetween to ensure that the desired reaction temperature can be maintained at the entrance to each reactor. The dehydrogenation unit may also include a regeneration zone to regenerate spent catalyst, and catalyst transfer equipment, such as pipes, vessels, and zones. The hydrocarbon may be contacted with the catalyst bed in either upward, downward, or radial flow fashion. Radial flow of the hydrocarbon through the catalyst bed is preferred for commercial scale reactors. The hydrocarbon may be in the liquid phase, a mixed vapor-liquid phase, or the vapor phase when it contacts the catalyst.

Hydrocarbons which may be dehydrogenated include dehydrogenatable hydrocarbons having from 2 to 30 or more carbon atoms including paraffins, alkylaromatics, naphthenes, and olefins. One group of hydrocarbons which can be dehydrogenated with the catalyst is the group of normal paraffins having from 2 to 30 or more carbon atoms. The catalyst is particularly useful for dehydrogenating paraffins having from 2 to 15 or more carbon atoms to the corresponding monoolefins or for dehydrogenating monoolefins having from 3 to 15 or more carbon atoms to the corresponding diolefins. The catalyst is especially useful in the dehydrogenation of $C_2$-$C_6$ paraffins, primarily propane and butanes, to monoolefins.

Dehydrogenation conditions include a temperature of from about 400° to about 900° C., a pressure of from about 0.01 to 10 atmospheres absolute, and a liquid hourly space velocity (LHSV) of from about 0.1 to 100 $hr^{-1}$. Generally, for normal paraffins, the lower the molecular weight, the higher the temperature required for comparable conversion. The pressure in the dehydrogenation zone is maintained as low as practicable, consistent with equipment limitations, to maximize the chemical equilibrium advantages.

The effluent stream from the dehydrogenation zone generally will contain unconverted dehydrogenatable hydrocarbons, hydrogen, and the products of dehydrogenation reactions. This effluent stream is typically cooled and passed to a hydrogen separation zone to separate a hydrogen-rich vapor phase from a hydrocarbon-rich liquid phase. Generally, the hydrocarbon-rich liquid phase is further separated by means of either a suitable selective adsorbent, a selective solvent, a selective reaction or reactions, or by means of a suitable fractionation scheme. Unconverted dehydrogenatable hydrocarbons are recovered and may be recycled to the dehydrogenation zone. Products of the dehydrogenation reactions are recovered as final products or as intermediate products in the preparation of other compounds.

The dehydrogenatable hydrocarbons may be admixed with a diluent material before, while, or after being passed to the dehydrogenation zone. The diluent material may be hydrogen, steam, methane, ethane, carbon dioxide, nitrogen, argon, and the like or a mixture thereof. Hydrogen and steam are the preferred diluents. Ordinarily, when hydrogen or steam is utilized as the diluent, it is utilized in amounts sufficient to ensure a diluent-to-hydrocarbon mole ratio of about 0.1:1 to about 40:1, with best results being obtained when the mole ratio range is about 0.4:1 to about 10:1. The diluent stream passed to the dehydrogenation zone will typically be recycled diluent separated from the effluent from the dehydrogenation zone in a separation zone.

A combination of diluents, such as steam with hydrogen, may be employed. When hydrogen is the primary diluent water or a material which decomposes at dehydrogenation conditions to form water such as an alcohol, aldehyde, ether, or ketone, for example, may be added to the dehydrogenation zone, either continuously or intermittently, in an amount to provide, calculated on the basis of equivalent water, about 1 to about 20,000 weight ppm of the hydrocarbon feed stream. About 1 to about 10,000 weight ppm of water addition gives best results when dehydrogenating paraffins have from 6 to 30 or more carbon atoms.

The dehydrogenation of hydrocarbons is an endothermic process. In a system employing a dehydrogenation catalyst only, it is typically necessary to add superheated steam at various points in the process or to intermittently remove and reheat the reaction stream between catalyst beds. Some processes have been developed which utilize a two-catalyst system with distinct beds or reactors of dehydrogenation or selective oxidation catalysts. The purpose of the selective oxidation catalysts is to selectively oxidize the hydrogen produced as a result of the dehydrogenation reaction with oxygen that had been added to the oxidation zone to generate heat internally in the process. The heat generated typically is sufficient to cause the reaction mixture to reach desired dehydrogenation temperatures for the next dehydrogenation step. The instant process may be accomplished in this previously mentioned system. If such a process is employed, the instant catalyst would comprise at least the dehydrogenation catalyst with another specific catalyst being used to accomplish the oxidation reaction.

The selective oxidation step, if utilized, uses the hydrogen which has been produced in the dehydrogenation step of the process to supply heat to the next dehydrogenation reaction section. To accomplish this, an oxygen-containing gas is first introduced into the reactor, preferably at a point adjacent to the selective oxidative catalyst section. The oxygen in the oxygen-containing gas is necessary to oxidize the hydrogen contained in the reaction stream. Examples of oxygen-containing gases which may be utilized to effect the selective oxidation of the hydrogen which is present will include air, oxygen, or air or oxygen diluted with other gases such as steam, carbon dioxide and inert gases such as nitrogen, argon, helium, etc. The amount of oxygen which is introduced to contact the process stream may range from about 0.01:1 to about 2:1 moles of oxygen per mole of hydrogen contained in the process stream at the point where oxygen is added to the process stream. In the selective oxidation reaction, the process stream which comprises unreacted dehydrogenatable hydrocarbon, dehydrogenated hydrocarbon, and hydrogen is reacted with oxygen in the presence of the selective steam oxidation/dehydrogenation catalyst whereby hydrogen is selectively oxidized to produce water and heat energy with very little of the oxygen reacting with the hydrocarbons.

The selective steam oxidation/dehydrogenation catalyst may be one that is useful for the selective oxidation of hydrogen in the presence of hydrocarbons. An example of such a catalyst is disclosed in U.S. Pat. No. 4,418,237. Alternatively, the catalyst used for the selective oxidation step may be identical to the catalyst utilized for the dehydrogenation step. Such catalysts or processes for their use are disclosed in U.S. Pat. Nos. 4,613,715 and 3,670,044.

The oxygen-containing reactant may be added to the instant process in various ways such as by admixing oxygen with a relatively cool hydrocarbon feed stream or with the steam diluent, or it may be added directly to the reactor independently of the feed hydrocarbons or the steam diluent. In addition, the oxygen-containing reactant can be added at one or more points in the reactor in such a fashion as to minimize local concentrations of oxygen relative to hydrogen in order to distribute the beneficial temperature rise produced by the selective hydrogen oxidation over the entire length of the dehydrogenation unit. The use of multiple injection points minimizes the opportunity for local build-up of the concentration of oxygen relative to the amount of hydrogen, thereby minimizing the opportunity for undesired reaction of the oxygen-containing gas with either feed or product hydrocarbons.

In some processes, a hydrocarbon feed stream comprising at least one paraffin is provided to a dehydrogenation unit comprising a moving bed reactor. The feed stream is contacted with a catalyst in the reactor under dehydrogenation conditions, and an effluent stream comprising at least one olefin is removed from the reactor. A portion of the catalyst in the reactor is periodically removed and the catalyst removed is replaced with fresh catalyst while continuing to operate the reactor. One or more of a flow rate of the feed stream, or a flow rate of the effluent is sensed. One or more of the flow rate of the feed stream, or the flow rate of the effluent is transmitted to a processor. One or more of the flow rate of the feed stream, or the flow rate of the effluent is analyzed to determine an activity rate. The activity rate and a cost of the catalyst are analyzed to determine at least one of an amount of catalyst to remove and replace, or a time to initiate removing and replacing the catalyst. The portion of the catalyst removed and replaced is adjusted to the determined amount of catalyst, or the catalyst is removed and replaced at the determined time.

The conversion across each reactor could be measured and/or detected by monitoring the feed and product (e.g., propane and propylene) at each reactor inlet and/or outlet. Alternatively or additionally, the reactor outlet temperature at each reactor could be measured, and/or the differential temperatures across each reactor could be measured. Another alternative, the differential pressure across each reactor could be monitored to determine the rate of screen fouling. These signals and/or data, as well as additional signals and/or data, could be sent to a processor, the optimal amount and timing of fresh catalyst addition to the system could be determined using one or more algorithms. The optimal amount and/or timing of the change could be executed manually by the operators, or the system could automatically change the set-point on a catalyst addition and removal system by changing catalyst valve outputs to adjust the frequency and/or amount of catalyst removal and fresh catalyst addition.

By the terms "about" or "approximately," we mean within 20% of the stated value, or within 10%, or within 5%, or within 3%, or within 1%.

SPECIFIC EMBODIMENTS

While the following is described in conjunction with specific embodiments, it will be understood that this description is intended to illustrate and not limit the scope of the preceding description and the appended claims.

A first embodiment of the invention is a process for dehydrogenation of a hydrocarbon feed comprising providing a hydrocarbon feed stream comprising at least one paraffin to a dehydrogenation unit comprising a moving bed reactor; contacting the feed stream with a catalyst in the reactor under dehydrogenation conditions, the catalyst having a particle size in a normal operating range; removing an effluent stream comprising at least one olefin from the reactor; and periodically removing a portion of the catalyst and replacing the portion of the catalyst removed with fresh catalyst while continuing to operate the reactor, wherein the portion of the catalyst removed has a particle size in the normal operating range. An embodiment of the invention is one, any or all of prior embodiments in this paragraph up through the first embodiment in this paragraph wherein the portion of the catalyst removed is between 5 wt % and 50 wt % of a total amount of the catalyst in the dehydrogenation unit. An embodiment of the invention is one, any or all of prior embodiments in this paragraph up through the first embodiment in this paragraph wherein the portion of the catalyst is removed on a predetermined time schedule. An embodiment of the invention is one, any or all of prior embodiments in this paragraph up through the first embodiment in this paragraph wherein the portion of the catalyst removed and replaced is between 10 wt % and 20 wt % of a total amount of the catalyst in the dehydrogenation unit. An embodiment of the invention is one, any or all of prior embodiments in this paragraph up through the first embodiment in this paragraph wherein the catalyst is removed and replaced every 60 to 120 days of operating time. An embodiment of the invention is one, any or all of prior embodiments in this paragraph up through the first embodiment in this paragraph wherein removing the portion of the catalyst and replacing the portion of the catalyst removed with fresh catalyst is stopped at a predetermined time before a planned shutdown of the reactor. An embodiment of the invention is one, any or all of prior embodiments in this paragraph up through the first embodiment in this paragraph wherein the predetermined time is 6 to 12 months before the planned shutdown of the reactor. An embodiment of the invention is one, any or all of prior embodiments in this paragraph up through the first embodiment in this paragraph wherein an operating time for the reactor is increased at least 20% over an operating time for the reactor without removing the portion of the catalyst and replacing the portion of the catalyst removed with fresh catalyst. An embodiment of the invention is one, any or all of prior embodiments in this paragraph up through the first embodiment in this paragraph wherein the portion of the catalyst removed is determined by one or more of measuring a production rate of the at least one olefin; measuring a consumption rate of the hydrocarbon feed; measuring a cost of the fresh catalyst replaced; measuring a temperature decrease across the reactor; or measuring a concentration of the at least one paraffin or the at least one olefin or both at an outlet of the reactor. An embodiment of the invention is one, any or all of prior embodiments in this paragraph up through the first embodiment in this paragraph, further comprising at least one of sensing at least one parameter of the process and generating a signal or data from the sensing; generating and transmitting a signal; or generating and transmitting data.

A second embodiment of the invention is a process for dehydrogenation of a hydrocarbon feed comprising providing a hydrocarbon feed stream comprising at least one paraffin to a dehydrogenation unit comprising a moving bed reactor; contacting the feed stream with a catalyst in the reactor under dehydrogenation conditions; removing an effluent stream comprising at least one olefin from the reactor; and periodically removing between 5 wt % and 50 wt % of a total amount of the catalyst in the dehydrogenation unit every 60 to 120 days of operating time and replacing the removed catalyst with fresh catalyst while continuing to operate the reactor. An embodiment of the invention is one, any or all of prior embodiments in this paragraph up through the second embodiment in this paragraph wherein the portion of the catalyst removed and replaced is between 10 wt % and 20 wt % of a total amount of the catalyst in the dehydrogenation unit. An embodiment of the invention is one, any or all of prior embodiments in this paragraph up through the second embodiment in this paragraph wherein removing the portion of the catalyst and replacing the portion of the catalyst removed with fresh catalyst is stopped at a predetermined time before a planned shutdown of the reactor. An embodiment of the invention is one, any or all of prior embodiments in this paragraph up through the second embodiment in this paragraph wherein the predetermined time is 6 to 12 months before the planned shutdown of the reactor. An embodiment of the invention is one, any or all of prior embodiments in this paragraph up through the second embodiment in this paragraph wherein an operating time for the reactor is increased at least 20% over an operating time for the reactor without removing the portion of the catalyst and replacing the portion of the catalyst removed with fresh catalyst. An embodiment of the invention is one, any or all of prior embodiments in this paragraph up through the second embodiment in this paragraph wherein the portion of the catalyst removed is determined by one or more of measuring a production rate of the at least one olefin; measuring a consumption rate of the hydrocarbon feed; measuring a cost of the fresh catalyst replaced; measuring a temperature decrease across the reactor; or measuring a concentration of the at least one molecule at an outlet of the reactor.

A third embodiment of the invention is a process for dehydrogenation of a hydrocarbon feed comprising providing a hydrocarbon feed stream comprising at least one paraffin to a dehydrogenation unit comprising a moving bed reactor; contacting the feed stream with a catalyst in the reactor under dehydrogenation conditions; removing an effluent stream comprising at least one olefin from the reactor; and periodically removing between 10 wt % and 20 wt % of a total amount of the catalyst in the dehydrogenation unit every 60 to 120 days of operating time and replacing the removed catalyst with fresh catalyst while continuing to operate the reactor. An embodiment of the invention is one, any or all of prior embodiments in this paragraph up through the third embodiment in this paragraph wherein removing the portion of the catalyst and replacing the portion of the catalyst removed with fresh catalyst is stopped 6 to 12 months before the planned shutdown of the reactor.

A fourth embodiment of the invention is a process for dehydrogenation of a hydrocarbon feed comprising providing a hydrocarbon feed stream comprising at least one paraffin to a dehydrogenation unit comprising a moving bed reactor; contacting the feed stream with a catalyst in the reactor under dehydrogenation conditions; removing an effluent stream comprising at least one olefin from the reactor; periodically removing a portion of the catalyst in the reactor and replacing the removed catalyst with fresh catalyst while continuing to operate the reactor; sensing one or more of a flow rate of the feed stream, or a flow rate of the effluent; transmitting one or more of the flow rate of the feed stream, or the flow rate of the effluent to a processor; analyzing one or more of the flow rate of the feed stream, or the flow rate of the effluent to determine an activity rate; analyzing the activity rate and a cost of the catalyst to determine at least one of an amount of catalyst to remove and replace, or a time to initiate removing and replacing the catalyst; and adjusting the portion of the catalyst removed and replaced to the determined amount of catalyst, or removing and replacing the catalyst at the determined time.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

What is claimed is:

1. A process for dehydrogenation of a hydrocarbon feed comprising:
providing a hydrocarbon feed stream comprising at least one paraffin to a dehydrogenation unit comprising a moving bed with radial flow in a reactor, wherein the reactor comprises screens that contain catalyst bed in the reactor;
contacting the hydrocarbon feed stream with a catalyst in the reactor under dehydrogenation conditions, the catalyst having a particle size in a normal operating range;
removing an effluent stream comprising at least one olefin from the reactor; and
periodically removing a portion of between 5 wt % and 50 wt % of a total amount of the catalyst in the dehydrogenation unit every 45 to 180 days of operating time and replacing the portion of the catalyst removed with fresh catalyst while continuing to operate the reactor, wherein the portion of the catalyst removed has a particle size in the normal operating range and is at least 1.2 mm.

2. The process of claim 1 wherein the portion of the catalyst removed and replaced is between 10 wt % and 20 wt % of the total amount of the catalyst in the dehydrogenation unit.

3. The process of claim 1 wherein the periodically removing and replacing the portion of the catalyst is conducted every 60 to 120 days of operating time.

4. The process of claim 1 wherein removing the portion of the catalyst and replacing the portion of the catalyst removed with fresh catalyst is stopped at a predetermined time before a planned shutdown of the reactor.

5. The process of claim 4 wherein the predetermined time is 6 to 12 months before the planned shutdown of the reactor.

6. The process of claim 1 wherein an operating time for the reactor is increased at least 20% over an operating time for the reactor without periodically removing the portion of between 5 wt % and 50 wt % of the total amount of the catalyst in the dehydrogenation unit every 45 to 180 days of operating time and replacing the portion of the catalyst removed with fresh catalyst.

7. The process of claim 1 wherein the portion of the catalyst removed is determined by one or more of: measuring a production rate of the at least one olefin; measuring a consumption rate of the hydrocarbon feed; measuring a cost of the fresh catalyst replaced; measuring a temperature decrease across the reactor; and measuring a concentration of the at least one paraffin or the at least one olefin or both at an outlet of the reactor.

8. The process of claim 1, further comprising at least one of:
sensing at least one parameter of the process and generating a signal or data from the sensing;
generating and transmitting a signal; and
generating and transmitting data.

9. A process for dehydrogenation of a hydrocarbon feed comprising:
providing a hydrocarbon feed stream comprising at least one paraffin to a dehydrogenation unit comprising a moving bed in a reactor, wherein the reactor comprises screens that contain catalyst bed in the reactor;
contacting the hydrocarbon feed stream with a catalyst in the reactor under dehydrogenation conditions;
removing an effluent stream comprising at least one olefin from the reactor; and
periodically removing a portion of between 5 wt % and 50 wt % of a total amount of the catalyst in the dehydrogenation unit every 60 and 120 days of operating time and replacing the removed catalyst with fresh catalyst while continuing to operate the reactor at a 20-100% longer time between shutdowns for screen cleaning compared to operating the reactor without periodically removing the portion of between 5 wt % and 50 wt % of the a total amount of the catalyst in the dehydrogenation unit every 60 to 120 days of operating time and replacing the portion of the removed catalyst with fresh catalyst.

10. The process of claim 9 wherein the portion of the catalyst removed and replaced is between 10 wt % and 20 wt % of the total amount of the catalyst in the dehydrogenation unit.

11. The process of claim 9 wherein removing the portion of the catalyst and replacing the portion of the catalyst removed with fresh catalyst is stopped at a predetermined time before a planned shutdown of the reactor.

12. The process of claim 11 wherein the predetermined time is 6 to 12 months before the planned shutdown of the reactor.

13. The process of claim 9 wherein an operating time for the reactor is increased at least 20% over an operating time for the reactor without removing the portion of the catalyst and replacing the portion of the catalyst removed with fresh catalyst.

14. The process of claim 9 wherein the portion of the catalyst removed is determined by one or more of: measuring a production rate of the at least one olefin; measuring a consumption rate of the hydrocarbon feed; measuring a cost of the fresh catalyst replaced; measuring a temperature decrease across the reactor; and measuring a concentration of the at least one paraffin or the at least one olefin or both at an outlet of the reactor.

15. A process for dehydrogenation of a hydrocarbon feed comprising:
providing a hydrocarbon feed stream comprising at least one paraffin to a dehydrogenation unit comprising a moving bed in a reactor, wherein the reactor comprises screens that contain catalyst bed in the reactor;
contacting the hydrocarbon feed stream with a catalyst in the reactor under dehydrogenation conditions;
removing an effluent stream comprising at least one olefin from the reactor; and
periodically removing a portion of between 10 wt % and 20 wt % of a total amount of the catalyst in the dehydrogenation unit every 60 and 120 days of operating time and replacing the removed catalyst with fresh catalyst while continuing to operate the reactor at a 20-100% longer time between shutdowns for screen cleaning compared to operating the reactor without periodically removing the portion of between 10 wt % and 20 wt % of the total amount of the catalyst in the dehydrogenation unit every 60 to 120 days of operating time and replacing the portion of the removed catalyst with fresh catalyst.

16. The process of claim 15 wherein removing the portion of the catalyst and replacing the portion of the catalyst removed with fresh catalyst is stopped 6 to 12 months before the planned shutdown of the reactor.

17. A process for dehydrogenation of a hydrocarbon feed comprising:
providing a hydrocarbon feed stream comprising at least one paraffin to a dehydrogenation unit comprising a moving bed in a reactor, wherein the reactor comprises screens that contain catalyst bed in the reactor;
contacting the hydrocarbon feed stream with a catalyst in the reactor under dehydrogenation conditions;
removing an effluent stream comprising at least one olefin from the reactor; and
periodically removing a portion of between 5wt % and 50 wt % of a total amount of the catalyst in the dehydrogenation unit every 60 to 120 days of operating time and replacing the portion of the catalyst removed with fresh catalyst while continuing to operate the reactor at a 20-100% longer time between shutdowns for screen cleaning compared to operating the reactor without periodically removing the portion of between 5 wt % and 50 wt % of the total amount of the catalyst in the dehydrogenation unit every 60 to 120 days of operating time and replacing the portion of the removed catalyst with fresh catalyst;
sensing one or more of a flow rate of the hydrocarbon feed stream, and a flow rate of the effluent stream;
transmitting one or more of the flow rate of the hydrocarbon feed stream, and a flow rate of the effluent stream to a processor;
analyzing one or more of the flow rate of the hydrocarbon feed stream, and the flow rate of the effluent stream to determine an activity rate of the catalyst;
analyzing the activity rate of the catalyst and a cost of the catalyst to determine at least one of an amount of catalyst to remove and replace, and a time to initiate removing and replacing the catalyst; and
adjusting the portion of the catalyst removed and replaced to a determined amount of catalyst, or removing and replacing the catalyst at a determined time.

* * * * *